(12) United States Patent
Gordon et al.

(10) Patent No.: US 7,094,753 B2
(45) Date of Patent: Aug. 22, 2006

(54) SOMATOSTATIN ANALOG AND USES THEREOF

(75) Inventors: Thomas D. Gordon, Medway, MA (US); Barry A. Morgan, Franklin, MA (US); Michael D. Culler, Hopkinton, MA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 164 days.

(21) Appl. No.: 10/302,431

(22) Filed: Nov. 21, 2002

(65) Prior Publication Data

US 2003/0153494 A1  Aug. 14, 2003

Related U.S. Application Data

(60) Provisional application No. 60/336,335, filed on Nov. 21, 2001.

(51) Int. Cl.
*A61K 38/00* (2006.01)
(52) U.S. Cl. .............................. 514/9; 514/16; 530/328; 530/329
(58) Field of Classification Search .................... 514/9, 514/12, 806; 930/22; 530/311; 424/1.1, 424/1.69
See application file for complete search history.

(56) References Cited

U.S. PATENT DOCUMENTS 4,853,371 A * 8/1989 Coy et al. ...................... 514/12

5,590,656 A * 1/1997 O'Dorisio et al. .......... 600/431

OTHER PUBLICATIONS

Murphy, W.A. et al., "Octapeptide analogs of somatostatin exhibiting greatly enhanced in vivo and in vitro inhibition of growth hormone secretion in the rat," Biochem. Biophys. Res. Comm., 1985, 132:922-928.
Colao, A. et al., "New medical approaches in pituitary adenomas," Hormone Research, 2000, 50:76-87.
Ferone, D. et al.,, "In vivo and in vitro effects of octreotide, quinagolide and cabergoline in four hyperprolactinaemic acromegalics: correlation with somatostatin and dopamine D-2 receptor scintigraphy," Clin. Endocrinology, 2001, 54:469-477.
Saveanu, G. et al., "BIM-23244, a somatostatin receptor subtype 2- and 5-selective analog with enhanced efficacy in suppression growth hormone (GH) from Octreotide-resistant human GH-secreting adenomas," J. Clin. Endocrinology and Metabolism, 2001, 86:140-145.
Shimon, I. et al., "Somatostatin receptor subtype specificity in human fetal pituitary cultures: differential role of SSTR2 and SSTR5 for growth hormone, thyroid-stimulating hormone, and prolactin regulation," J. Clin. Investigation, 1997, 99:789-798.

* cited by examiner

*Primary Examiner*—Bruce R. Campell
*Assistant Examiner*—B. Dell Chism
(74) *Attorney, Agent, or Firm*—Yankwich & Associates; Brian R. Morrill; Alan F. Feeney

(57) ABSTRACT

Claimed is a somatostatin agonist according to formula (I),

D-Phe-c(Cys-Tyr(I)-D-Trp-Lys-Val-Cys)-Thr-$NH_2$,     (I)

or a pharmaceutically acceptable salt thereof, and uses thereof.

1 Claim, No Drawings

SOMATOSTATIN ANALOG AND USES THEREOF

CROSS REFERENCE TO RELATED APPLICATIONS

This application claims the benefit of the filing date of U.S. provisional application, U.S. Ser. No. 60/336,335, filed Nov. 21, 2001, hereby incorporated by reference.

BACKGROUND OF THE INVENTION

Somatostatin (SRIF), a tetradecapeptide discovered by Brazeau et al., has been shown to have potent inhibitory effects on various secretory processes in tissues such as pituitary, pancreas and gastrointestinal tract. SRIF also acts as a neuromodulator in the central nervous system. These biological effects of SRIF, all inhibitory in nature, are elicited through a series of G protein coupled receptors, of which five different subtypes have been characterized (SSTR-1 to SSTR-5). These five subtypes have similar affinities for the endogenous SRIF ligands but have differing distribution in various tissues. SRIF binds to each of the five distinct receptor (SSTR) subtypes with relatively high affinity.

SRIF produces a variety of effects, including modulation of hormone release, e.g., growth hormone, glucagon, insulin, amylin, and neurotransmitter release. Some of these effects have been associated with its binding to a specific SRIF receptor. For example, the inhibition of growth hormone has been attributed to the somatostatin type-2 receptor ("SSTR-2") (Raynor, et al., Molecular Pharmacol. 43:838 (1993); Lloyd, et al., Am. J. Physiol. 268:G102 (1995)), while the inhibition of insulin has been attributed to the somatostatin type-5 receptor ("SSTR-5") (Coy, et al. 197: 366–371 (1993)). Activation of types 2 and 5 have been associated with growth hormone suppression and more particularly with GH secreting adenomas (acromegaly) and TSH secreting adenomas. Activation of type 2 but not type 5 has been associated with treating prolactin secreting adenomas.

As is well known to those skilled in the art, SRIF and analogs thereof are useful in the treatment of a great variety of diseases and/or conditions. An exemplary but by no means exhaustive list of such diseases and/or conditions would include: Cushings Syndrome (see Clark, R. V. et al, Clin. Res. 38, p. 943A, 1990); gonadotropinoma (see Ambrosi B., et al., Acta Endocr. (Copenh.) 122, 569–576, 1990); hyperparathyroidism (see Miller, D., et al., Canad. Med. Ass. J., Vol. 145, pp. 227–228, 1991); Paget's disease (see, Palmieri, G. M. A., et al., J. of Bone and Mineral Research, 7, (Suppl. 1), p. S240 (Abs. 591), 1992); VIPoma (see Koberstein, B., et al., Gastroenterology, 28, 295–301, 1990 and Christensen, C., Acta Chir. Scand. 155, 541–543, 1989); nesidioblastosis and hyperinsulinism (see Laron, Z., Israel J. Med. Sci., 26, No. 1, 1–2, 1990, Wilson, D. C., Irish J. Med. Sci., 158, No. 1, 31–32, 1989 and Micic, D., et al., Digestion, 16, Suppl. 1.70. Abs. 193, 1990); gastrinoma (see Bauer, F. E., et al., Europ. J. Pharmacol., 183, 55 1990); Zollinger-Ellison Syndrome (see Mozell, E., et al., Surg. Gynec. Obstet., 170, 476–484, 1990); hypersecretory diarrhea related to AIDS and other conditions (due to AIDS, see Cello, J. P., et al., Gastroenterology, 98, No. 5, Part 2, Suppl., A163 1990; due to elevated gastrin-releasing peptide, see Alhindawi, R., et al., Can. J. Surg., 33, 139–142, 1990; secondary to intestinal graft vs. host disease, see Bianco J. A., et al., Transplantation, 49, 1194–1195, 1990; diarrhea associated with chemotherapy, see Petrelli, N., et al., Proc. Amer. Soc. Clin. Oncol., Vol. 10, P 138, Abstr. No. 417 1991); irritable bowel syndrome (see O'Donnell, L. J. D., et al., Aliment. Pharmacol. Therap., Vol. 4., 177–181, 1990); pancreatitis (see Tulassay, Z., et al., Gastroenterology, 98, No. 5, Part 2, Suppl., A238, 1990); Crohn's Disease (see Fedorak, R. N., et al., Can. J. Gastroenterology, 3, No. 2, 53–57, 1989); systemic sclerosis (see Soudah, H., et al., Gastroenterology, 98, No. 5, Part 2, Suppl., A129, 1990); thyroid cancer (see Modigliani, E., et al., Ann., Endocr. (Paris), 50, 483–488, 1989); psoriasis (see Camisa, C., et al., Cleveland Clinic J. Med., 57 No. 1, 71–76, 1990); hypotension (see Hoeldtke, R. D., et al., Arch. Phys. Med. Rehabil., 69, 895–898, 1988 and Kooner, J. S., et al., Brit. J. Clin. Pharmacol., 28, 735P–736P, 1989); panic attacks (see Abelson, J. L., et al., Clin. Psychopharmacol., 10, 128–132, 1990); sclerodoma (see Soudah, H., et al., Clin. Res., Vol. 39, p. 303A, 1991); small bowel obstruction (see Nott, D. M., et al., Brit. J. Surg., Vol. 77, p. A691, 1990); gastroesophageal reflux (see Branch, M. S., et al., Gastroenterology, Vol. 100, No. 5, Part 2 Suppl., p. A425, 1991); duodenogastric reflux (see Hasler, W., et al., Gastroenterology, Vol. 100, No. 5, Part 2, Suppl., p. A448, 1991); Graves' Disease (see Chang, T. C., et al., Brit. Med. J., 304, p. 158, 1992); polycystic ovary disease (see Prelevic, G. M., et al., Metabolism Clinical and Experimental, 41, Suppl. 2, pp 76–79, 1992); upper gastrointestinal bleeding (see Jenkins, S. A., et al., Gut., 33, pp. 404–407, 1992 and Arrigoni, A., et al., American Journal of Gastroenterology, 87, p. 1311, (abs. 275), 1992); pancreatic pseudocysts and ascites (see Hartley, J. E., et al., J. Roy. Soc. Med., 85, pp. 107–108, 1992); leukemia (see Santini, et al., 78, (Suppl. 1), p. 429A (Abs. 1708), 1991); meningioma (see Koper, J. W., et al., J. Clin. Endocr. Metab., 74, pp. 543–547, 1992); and cancer cachexia (see Bartlett, D. L., et al., Surg. Forum., 42, pp. 14–16, 1991).

The variable sensitivity of acromegalic patients to the current clinically available SRIF agonists, octreotide and lanreotide, has already been underlined. (Ann Intern Med. 117:711–718 (1992); 3J Clin Endocrinol Metab 71:391–397 (1990)). An improved patient response has been reported using the long-lasting depot formulations of either octreotide or lanreotide (Flogstad A K, et al. 1997, J Clin Endocrinol Metab. 82:23–28; Caron P, et al., 1997, J Clin Endocrinol Metab. 82:18–22.). In these reports 70–80% of the acromegalic patients were considered to be controlled with these long-lasting SRIF agonists formulations. Such data were, in fact, biased due to preselection of patients already known to be responders through previous sc administration of octreotide. When such preselection is eliminated, the percentage of patients who achieve mean GH levels less than 2.5 µg/L with slow release lanreotide has been demonstrated in recent studies to be 50–60% (al-Maskari M, et al., 1996, Clin Endocrinol (Oxf). 45:415–421.). Thus, about 40–50% of acromegalic patients remain partially or poorly controlled under the current SRIF agonist treatments.

In acromegaly, a quantitative loss of SRIF receptors explains the very poor or absent GH suppression in response to acute administration of octreotide or SRIF in 3 of 17 cases (Ikuyama S, et al, 1985 J Clin Endocrinol Metab. 61:666–67;. Reubi J C, Landolt A M, 1989, J Clin Endocrinol Metab. 68:844–850). Such a loss of SRIF receptors is seldom encountered and cannot fully explain the partial GH-suppressive effects of octreotide and lanreotide in vivo. In a subsequent study of 37 GH-secreting tumors, the density of SRIF receptors was poorly correlated to the GH-suppressive effects of octreotide in vivo (Bertherat J, et al. 1993, J Clin Endocrinol Metab 77:1577–1583.). Another hypothesis that could explain the partial GH-suppressive effects of octreotide or lanreotide in certain acromegalic patients comes from the identification of 5 SSTR subtypes (Patel Y C, Srikant C B, 1994, Endocrinology. 135:2814–2817.). In human tumors of various origins, specific patterns of SSTR subtype expression have been described (Eden P A, Taylor J E. 1993, Life Sci. 53:85–90; Schaer J C, et al., 1997, Int J Cancer. 70:530–537.). Among the GH-secreting adenomas, a consistent pattern of SSTR2 and SSTR5 mRNA expression has been identified (Greenman Y, Melmed S. 1994, J Clin Endocrinol Metab. 78:398–403; Greenman Y, Melmed S. 1994, J Clin Endocrinol Metab. 79:724–729; Miller G M, et al., 1995, J Clin Endocrinol Metab. 4:1386–1392; Murabe H, et al. 1996, J Neuroendocrinol. 8:605–610; Nielsen S, et al. 1998, J Clin Endocrinol Metab. 83:2997–3000; Panetta R, Patel Y C. 1995, Life Sci. 56:333–342; Reubi J C, et al., 1994, Cancer Res. 54:3455–3459). Previous studies have shown an inhibition of GH release using SSTR2-preferential agonists. However, an SSTR5-preferential agonist has also been shown to induce a significant inhibition of GH release in 7 of 15 GH-secreting tumors (Jaquet P, et al. 2000, J Clin Endocrinol Metab. 85:781–792) and 6 of 7 GH-secreting tumors (Shimon I, et al., 1997, J Clin Invest. 100:2386–2392; Shimon I, et al. 1997, J Clin Invest. 4:789–798.).

These data implicate the SSTR5 subtype in the inhibition of GH release in certain tumors. This hypothesis is confirmed in our study using the bispecific SSTR2- and SSTR5-preferential compound of formula (I). Indeed, when the tumors were only responsive to SSTR2 preferential analogs, this compound was unable to produce any additional effect on inhibition of GH release compared with octreotide. However, in the tumors equally responsive to both SSTR2 and SSTR5 agonists, the compound of formula (I) was significantly more potent than octreotide in the suppression of GH and PRL secretion. The comparison between dose-response inhibition of GH release with the compound of formula (I) and SRIF-14 showed that this compound more closely mimicked the effects of native SRIF by acting via both SSTR2 and SSTR5 subtypes.

From our data, two classes of tumors emerged among the GH-secreting adenomas. The first was a series of tumors characterized by high sensitivity to SRIF-14 and SSTR2-preferential agonists. These tumors presented the highest level of SSTR2 mRNA expression and had the highest GH-suppressive effect with octreotide. In the second class of tumors, the level of SSTR2 mRNA was low, and octreotide produced only partial inhibition of GH release. SRIF-14 was nevertheless able to suppress GH release, with a maximal suppressive effect similar to that of the first class of tumors, but at a 10-fold higher concentration. The presence of high levels of SSTR5 mRNA was associated with a potent suppressive effect of Compound B on GH release, more efficacious than that of the SSTR2 analogs. In these tumors, the bispecific SSTR2 and SSTR5 compound of formula (I) induced a suppression of GH release identical to that achieved by native SRIF. Thus in tumors deficient in the SSTR2 subtype presenting with a high SSTR5/SSTR2 ratio there may be a rescue through the SSTR5 subtype that mediates the suppression of GH release.

Other indications associated with activation of the SRIF receptor subtypes are inhibition of insulin and/or glucagon and more particularly diabetes mellitus, angiopathy, retinopathy, proliferative retinopathy, dawn phenomenon and nephropathy; inhibition of gastric acid secretion and more particularly peptic ulcers, enterocutaneous and pancreaticocutaneous fistula, Dumping syndrome, watery diarrhea syndrome, acute or chronic pancreatitis and gastrointestinal hormone secreting tumors; treatment of cancer such as hepatoma; inhibition of angiogenesis, treatment of inflammatory disorders such as arthritis; chronic allograft rejection; angioplasty; preventing graft vessel and gastrointestinal bleeding.

Additionally, the following references disclose the use of certain somatostatin analogs for the indications noted: U.S. Pat. No. 4,853,371—inhibiting the secretion of growth hormone, insulin, glucagon and pancreatic exocrine secretion; U.S. Pat. No. 5,147,856—restenosis; U.S. Pat. No. 5,411,943—hepatoma; U.S. Pat. No. 5,073,541—lung cancer; U.S. Pat. No. 5,504,069—inhibiting the accelerated growth of a solid tumor; U.S. Pat. No. 5,688,418—prolonging survival of pancreatic cells; U.S. patent application Ser. No. 08/089,410 filed Jul. 9, 1993—melanoma; U.S. patent application Ser. No. 08/854,941 filed May 13, 1997—decreasing body weight; U.S. patent application Ser. No. 08/854,943 filed May 13, 1997—insulin resistance and Syndrome X; U.S. patent application Ser. No. 08/855,311 filed May 13, 1997—hyperlipidemia; U.S. patent application Ser. No. 08/440,061 filed May 12, 1995—hyperamylinemia; U.S. patent application Ser. No. 08/852,221 filed May 7, 1997—hyperprolactinemia and prolactinomas; International Patent Application No. PCT/US97/14154—fibrosis.

It is preferred to have an analog which is selective for the specific SRIF receptor subtype or subtypes responsible for the desired biological response, thus, reducing interaction with other receptor subtypes which could lead to undesirable side effects. Further, because of the short half-life of native SRIF, various SRIF analogs have been developed, e.g., for the treatment of acromegaly, (Raynor, et al., Molecular Pharmacol. 43:838 (1993)).

SUMMARY OF THE INVENTION

In one aspect the invention relates to a peptide according to formula (I):

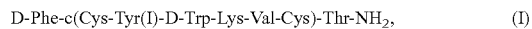

D-Phe-c(Cys-Tyr(I)-D-Trp-Lys-Val-Cys)-Thr-NH$_2$,  (I)

or a pharmaceutically acceptable salt thereof.

The compound of formula (I) is useful for the same uses as SRIF. Thus another aspect the invention features a method of binding one or more of human somatostatin subtype receptors -1, -2, -3 and -5, which comprises the step of administering the compound of formula (I) or a pharmaceutically acceptable salt thereof to a recipient in need thereof. Preferably said compound of formula (I) selectively binds to somatostatin subtype receptors -2 and -5.

In a preferred embodiment of the immediately foregoing method is featured a method of eliciting a somatostatin agonist effect, which comprises the step of administering the compound of formula (I) or a pharmaceutically acceptable salt thereof to a recipient in need thereof.

In a more preferred embodiment of the immediately foregoing method is featured a method of treating a disease or condition in a human or other animal in need thereof, which comprises the step of administering the compound of formula (I) or a pharmaceutically acceptable salt thereof to said human or other animal, wherein said disease or condition is selected from the group consisting of Cushings Syndrome, gonadotropinoma, hyperparathyroidism, Paget's disease, VIPoma, nesidioblastosis, hyperinsulinism, gastrinoma, Zollinger-Ellison Syndrome, hypersecretory diarrhea related to AIDS and other conditions, irritable bowel syndrome, pancreatitis, Crohn's Disease, systemic sclerosis, thyroid cancer, psoriasis, hypotension, panic attacks, sclerodoma, small bowel obstruction, gastroesophageal reflux, duodenogastric reflux, Graves' Disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia prolactinomas diabetic neuropathy, macular degeneration, hypercalcemia of malignancy, postprandial portal hypertension, and complications of portal hypertension.

In yet a more preferred embodiment of the immediately foregoing method is featured a method of treating a disease or condition in a human or other animal in need thereof, which comprises the step of administering the compound of formula (I) or a pharmaceutically acceptable salt thereof to said human or other animal, wherein said disease or condition is acromegaly.

In another more preferred embodiment of the immediately foregoing method is featured a method of treating a disease or condition in a human or other animal in need thereof, which comprises administering a compound of formula (I), or a pharmaceutically acceptable salt thereof, to said mammal, wherein said disease or condition is selected from the group consisting of Grave's opthalmopathy, non-functioning pituitary tumors, angiogenesis, inflammation and inflammatory diseases, carcinoid syndrome, carcinoid tumors, retinopathy, and macular degeneration.

The nomenclature for the somatostatin receptor subtypes is in accordance with the recommendations of IUPHAR, in which SSTR-4 refers to the receptor originally cloned by Bruno et al., and SSTR-5 refers to the receptor cloned by O'Carroll et al.

With the exception of the N-terminal amino acid, all abbreviations (e.g., D-Phe in formula (I)) of amino acids in this disclosure stand for the structure of —NH—CH(R)—CO—, wherein R in the immediately foregoing formula is the side chain of an amino acid (e.g., $CH_3$ for Ala). For the N-terminal amino acid, the abbreviation stands for the structure of $(R^1R^2)$—N—CH(R)—CO—, wherein R is a side chain of an amino acid and $R^1$ and $R^2$ are as defined herein.

Abbreviations of the common amino acids are in accordance with the recommendations of IUPAC-IUB. The following are abbreviations of certain α-amino acids as may appear herein:

| | |
|---|---|
| Cys = | cysteine |
| Lys = | lysine; |
| Phe = | phenylalanine; |
| Thr = | threonine |
| Trp = | tryptophan; |
| Tyr = | tyrosine |
| Tyr(I) = | 3-iodotyrosine |
| Val = | valine |

Additional abbreviations used herein include:
DBU, 1,8-diazabicyclo(5.4.0)undec-7-ene;
DCM, dichloromethane;
DIC, dicyclohexylcarbodiimide;
DIEA, diisopropylethylamine;
DMF, dimethylformamide;
Fmoc, 9-Fluorenylmethoxycarbonyl
MTBD, 1,3,4,6,7,8-Hexahydro-1-methyl-2H-pyrimido(1,2-a)pyrimidine;
NPS, 2-nitrophenylsulfonyl;
TBTU, O-Benzotri-azol-1-yl-N,N,N',N'-tetramethyluronium tetrafluoroborate; and
TFA, trifluoroacetic acid.

A compound of the present invention or pharmaceutically acceptable salt thereof can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders, granules and the like. In such solid dosage forms, the active compound is admixed with at least one inert pharmaceutically acceptable carrier such as sucrose, lactose, or starch. Such dosage forms can also comprise, as is normal practice, additional substances other than such inert diluent, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 25 μg/kg/day to 100 mg/kg/day of body weight daily are administered as a single dose or divided into multiple doses to humans and other animals, e.g., mammals, to obtain the desired therapeutic effect.

A preferred general dosage range is 250 μg/kg/day to 5.0 mg/kg/day of body weight daily which can be administered as a single dose or divided into multiple doses.

Further, a compound of the present invention or pharmaceutically acceptable salt thereof can be administered in a sustained release composition such as those described in the following patents. Among those formulations, 14-day or 28-day slow release formulations will be preferred. U.S. Pat. No. 5,672,659 teaches sustained release compositions comprising a peptide and a polyester. U.S. Pat. No. 5,595,760 teaches sustained release compositions comprising a peptide in a gelable form. U.S. Pat. No. 5,821,221 teaches polymeric sustained release compositions comprising a peptide and chitosan. U.S. Pat. No. 5,916,883 teaches sustained release compositions comprising a peptide and cyclodextrin. International Patent Application No. PCT/US99/01180, (publication no. WO 99/38536, Aug. 5, 1999), teaches absorbable sustained release compositions of a peptide. The contents of the foregoing patents and applications are incorporated herein by reference.

The use of immediate or of sustained release compositions depends on the type of indications targeted. If the indication consists of an acute or over-acute disorder, a treatment with an immediate form will be preferred over the same with a prolonged release composition. On the contrary, for preventive or long-term treatments, a prolonged release composition will generally be preferred.

DETAILED DESCRIPTION OF THE INVENTION

One skilled in the art can, based on the description herein, utilize the present invention to its fullest extent. The following specific embodiments are, therefore, to be construed as merely illustrations of the invention and are not meant to be construed as limiting the full scope of the invention in any way.

Synthesis

A compound of the present invention, e.g., a compound of formula (I), can be and was synthesized on Rink Amide MBHA resin, (4-(2',4'-dimethyoxyphenyl-Fmoc-aminomethyl)-phenoxyacetamido-norleucyl-MBHA resin), using a standard solid phase protocol of Fmoc chemistry and cleaved with a trifluoroacetic acid (TFA)/water/triisopropylsilane (TIPS) (90%/8.5%/1.5% ) mixture. The peptide was cyclized in a solution of 4% acetic acid in water by adding 1.5 equivalents of iodine in a methanol solution (20 mg/mL methanol) and purified by using a prep HPLC with a C18 silica column, eluting with acetonitrile/0.1% TFA and water/0.1% TFA buffers. Homogeneity was assessed by analytical HPLC and mass spectrometry.

The Fmoc protected amino acids used for the synthesis of the peptide were Fmoc-Thr(OtBu)-OH, Fmoc-Cys(Acm)-OH, Fmoc-Val-OH, Fmoc-Lys(Boc)-OH, Fmoc-D-Trp-OH, Fmoc-D-Phe-OH, which were purchased from Nova Biochem (San Diego, Calif.) and Fmoc-3-Iodo-Tyr-OH, which was purchased from Advanced ChemTech (Louisville, Ky.).

EXAMPLE 1

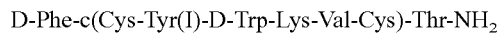

D-Phe-c(Cys-Tyr(I)-D-Trp-Lys-Val-Cys)-Thr-NH$_2$ 2.0 grams of Rink Amide MBHA resin (0.65 mmole/g) (MidWest Bio-Tech, Fishers, Ind.) were swelled in N,N-dimethylformamide (DMF) 3 times for about 10 minutes each time. The resin was then treated with 25% piperidine in DMF for 2× about 10 minues and washed with DMF. To the resin were added Fmoc-Thr(OtBu)-OH (3 eq., 1.548 g), 2-(1H-benzotriazole-1-yl)-1,1,3,3,-tetramethyluronium tetrafluoroborate (TBTU) (1.236 g), N-hydroxybenzotriazole (HOBt) (0.589 g), DIEA (0.891 mL) and DMF (11 mL). The mixture was shaken at room temperature for about 1 hour. The above deprotection and coupling steps were repeated with successive Fmoc amino acids of the desired peptide. After finishing the deprotection of the Fmoc group on the last amino acid, Fmoc-D-Phe, the resin was washed with DMF and dichloromethane (DCM) and dried in vaccuo.

For the cleavage step, the dry resin was treated with TFA/water/TIPS (54 mL/5.1 mL/0.9 mL) at room temperature for about 2 hours. The resin was filtered off, washed with 5 mL of TFA, and the filtrate was concentrated under reduced pressure. To the residue was added 200 mL of ether. The precipitate was filtered off, washed with ether, and dried in vaccuo. This crude linear peptide was dissolved in 600 mL of 4% acetic acid aqueous solution. To the solution was slowly added 12.95 mL of iodine solution in methanol (20 mg I$_2$/mL methanol). The solution was stirred at about 45° C. for about 30 minutes. The solution was cooled to room temperature and quenched with 2% sodium thiosulfate aqueous solution. The resulting solution was applied to a prep HPLC (C18 column) for purification. The column was eluted with a gradient of buffer A (0.1% TFA in water) and buffer B (0.1% TFA in 20% water and 80% acetonitrile). The fractions were checked by analytical HPLC and the fractions containing pure peptide were pooled and lyophilized to dryness. 589 mg of the desired peptide was obtained with purity of >99%. M. W.calc.=1172.2, M.W. observed (MS-ES)=1171.4.

The compound of formula (I) was synthesized and isolated as described above. However, one of skill in the art will readily appreciate that the synthesis of a peptide such as the compound of formula (I) would be readily achieved by a number of known synthetic methods such as, e.g., those described in the various references cited herein.

Functional Expression of the Cloned Human Somatostatin Receptors

The genomic clones containing the human somatostatin receptors (hSSTR-1 to hSSTR-5) (Yamada, Y., et al. al., *Proc. Natl. Acad. Sci. USA*. 1992, 89, 251–255; Yasuda, K., et al., *J. Biol. Chem*. 1992, 267, 20422–20428; Yamada, Y., et al., *Mol. Pharmacol*. 1992, 42, 2136–2142; Rohrer, L., et al., *Proc. Natl. Acad. Sci. USA*. 1993, 90, 4196–4200.) were kindly provided by Dr. Graeme I. Bell of the University of Chicago. The hSSTR-1, hSSTR-2, hSSTR-3, hSSTR-4 and hSSTR-5 cDNAs were isolated as a 1.5-kb PstI-XmnI fragment, 1.7-kb BamHI-HindIII fragment, 2.0-kb NcoI-HindIII fragment, 1.4-kb NheI-NdeI fragment, and a 1.2-kb HindIII-XbaI fragment, respectively, each containing the entire coding region of the full-length receptors. These fragments were independently subcloned into the corresponding restriction endonuclease sites in the mammalian expression vector pCMV5, downstream from the human cytomegalovirus (CMV) promoter, to produce the expression plasmids pCMV5/hSSTR-1, pCMV5/hSSTR-2, pCMV5/hSSTR-3, pCMV5/hSSTR-4 and pCMV5/hSSTR-5. For transfection into CHO-K1 cells, a plasmid, pRSV-neo (American Type Culture Collection, Rockville, Md.), carrying the neomycin mammalian cell selectable marker was added.

Receptor Expression and Transfection

Transfections were performed by the calcium phosphate method. CHO-K1 cells were maintained in α-minimum essential medium (α-MEM; Gibco) supplemented with 10% fetal calf serum and transfected with each of the expression plasmids using calcium phosphate precipitation. Clones that had inherited the expression plasmid were selected in α-MEM supplemented with 500 μg mL$^{-1}$ of geneticin (G418; Gibco). Independent CHO-K1 clones were picked by glass-ring cloning and expanded in culture in the selective media. Membranes were prepared from the isolated clones and hSSTR expression was initially assessed for binding with ($^{125}$I)Tyr$^{11}$-SIF and ($^{125}$I)MK-678 (for SSTR-2).

Radioligand Binding Assays

Cell membranes of the 5 cells types were obtained from homogenates (Polytron setting 6, 15 sec) of the corresponding CHO-K1 cells, in ice-cold Tris-HCl (50 mM) and centrifuged (39000 g, 2×10 minutes), with an intermediate resuspension in fresh buffer. The final pellets were resuspended in Tris-HCl (10 mM) for assay. Aliquots of the membranes were incubated (30 minutes at 37° C.) with 0.05 nM ($^{125}$I)Tyr$^{11}$-SRIF (types 1,3,4,5) or ($^{125}$I)MK-678 (type 2) in 50 nM HEPES (pH 7.4) containing BSA (10 mg mL$^{-1}$); MgCl$_2$ (5 mM), Trasylol (200 kIU mL$^{-1}$), bacitracin (0.02 mg mL$^{-1}$), and phenylmethanesulfonyl fluoride (0.02 mg mL$^{-1}$). The final assay volume was 0.3 mL and incubations were terminated by rapid filtration through GF/C filters pre-soaked in 0.3% poly(ethylenimine) using a Brandel rapid filtration module. Each tube and filter was then washed with aliquots of cold buffer (3×5 mL).

Specific binding is defined as the total radioligand bound minus that bound in the presence of 1.0 μM SRIF. The following total radioligand binding and non-specific binding (nsb) values were typically obtained with these assay systems: hSSTR-1, 7000 cpm total versus 3500 cpm nsb; hSSTR-2, 9000 cpm total versus 1000 cpm nsb; hSSTR-3, 8000 cpm total versus 1000 cpm nsb; hSSTR-4, 6000 cpm total versus 3500 cpm nsb; and hSSTR-5, 7500 cpm total versus 3500 cpm nsb. The binding affinities are expressed as K$_i$ values±SEM (nM) for each of the five receptor subtypes. Ki values derived for the compound of formula (I) are provided in Table 2.

Patients

Ten acromegalic patients (seven women and three men), aged 26–62 years, presenting with macroadenoma were studied. Their endocrine status and the neuroradiological characterization of the pituitary adenomas were documented before treatment. Basal GH levels were the mean of three random samples obtained between 0800–0900 h. The basal IGF-I value was evaluated under fasting conditions between 0800–0900 h. Magnetic resonance imaging revealed adenomas with a maximal 11- to 42-mm diameter. SRIF agonist sensitivity was assessed by an acute test using a single 200 μg injection of octreotide (Sandostatin, Novartis, Basel, Switzerland). Sensitivity to somatostatin analogs was expressed as the percent decrease in GH from the basal value to the mean GH values 2–6 h after octreotide injection. According to the test results, five patients were considered full octreotide responders (mean GH suppression, 79±7%), whereas the other five cases were considered partial octreotide responders (mean GH suppression, 33±6%). All patients underwent transsphenoidal surgery. The clinical endocrine and tumoral status of each patient is summarized in Table 1.

Hormone Assays

GH and PRL were measured using commercial immunoradiometric kits (Immunotech, Marseilles, France). Normal GH values ranged from 0.2–2.4 μg/L; normal PRL values ranged from 1–24 μg/L in women and from 1–17 μg/L in men. After an ethanol-acid extraction, the plasma IGF-I assay was performed using the IGF-I RIA kit from Nichols Institute Diagnostics (San Juan Capistrano, Calif.).

Detection of SSTRs

Total RNA was extracted from 30–60 mg tissue from each tumor using the SV total RNA isolation system (Promega Corp., Lyon, France). The RNA samples were subsequently treated with 30 U ribonuclease-free deoxyribonuclease I (Roche, Mannheim, Germany). Total RNA was reverse transcribed into complementary DNA using 1 μg hexamers (Pharmacia Biotech, Orsay, France) and Moloney murine leukemia virus reverse transcriptase, as described by the manufacturer. The 5'-exonuclease (Taq Man) assay, which produces a direct proportional readout for the progression of PCR reactions, was used to quantify the SSTRs mRNA (Perkin-Elmer. 1995 (Taq Man TM) probe design, synthesis, and purification. Foster City: Applied Biosystems). The details of reaction conditions, the primers used, and the quantification calculation for SSTR2 and SSTR5 mRNA were described previously (Jaquet P, et al. 2000, J Clin Endocrinol Metab. 85:781–792). The results were expressed as picograms of SSTR per picograms glyceraldehyde-3-phosphate dehydrogenase (GAPDH).

Cell Culture Studies

A portion of each tumor obtained at surgery was dissociated by mechanical and enzymatic methods. Depending on the tumor, 4–90×10$^6$ isolated cells were obtained. Tumor cells were initially cultured in DMEM supplemented with 10% FCS for 3 days. On day 3, the cells were washed and plated in multiwell culture dishes (Costar 3524, Brumath, France) coated with extracellular matrix from bovine endothelial corneal cells as previously described (Jaquet P, et al., 1985, Horm Res. 22:153–163.) at a density of 2×10$^4$ cells/well. When they were attached to the matrix on days 5–8, depending on the culture, the medium was removed and replaced with DMEM supplemented with 2% FCS, antibiotics, transferrin, and selenium as previously described (Jaquet P, et al., 1985, Horm Res. 22:153–163.). The effects of various doses of SRIF-14; octreotide; a SSTR2- preferential compound, Compound A; a SSTR5-preferential compound Compound B; and the SSTR2- and SSTR5-selective compound of formula (I), on the inhibition of GH and PRL release were measured over an 8-h period between days 5–8 of culture. Each drug concentration was tested in quadruplicate.

Products

SRIF-14 was purchased from Sigma (Saint-Quentin Fallavier, France). Octreotide was supplied by Novartis (Basel, Switzerland). The Compounds A and B were provided by Biomeasure, Inc. (Milford, Mass.). The native SRIF and SRIF analogs were dissolved in 0.01 mol/L acetic acid containing 0.1% purified serum albumin (Life Technologies, Inc., Cergy-Pontoise, France). The drugs were stored at −80 C. as 10$^{-3}$ mol/L solutions. For each experiment, fresh working solutions were prepared from a new aliquot.

Statistics

The results are presented as the mean±SEM. Statistical significance between two unpaired groups was determined by the Mann-Whitney test. To measure the strength of association between the pairs of variables without specifying dependencies, Spearman order correlation's were used. P<0.05 was considered significant for all tests.

TABLE 1

Clinical characterization and RT-PCR quantification of SSTR2 and SSTR5 mRNAs in acromegalic patients

| Case No. | Sex | Age (yr.) | Tumor Size (mm)[a] | GH (μg/L) Basal | GH (μg/L) Under Octreotide[c] | PRL (μg/L) | IGF-I (μg/L) | SSTR SSTR2 | SSTR subtype[b] SSTR5 |
|---|---|---|---|---|---|---|---|---|---|
| A1 | M | 53 | 11 | 11 | 1 (91) | 11 | 1171 | 371 | 555 |
| A2 | F | 39 | 15 | 22 | 4 (82) | 17 | 885 | 366 | 744 |
| A3 | F | 44 | 13 | 109 | 26 (76) | 12 | 881 | 153 | 129 |
| A4 | M | 32 | 15 | 141 | 36 (75) | 2 | 1010 | 127 | 130 |
| A5 | F | 40 | 39 | 47 | 12 (75) | 17 | 1008 | 93 | 75 |
| A6 | F | 62 | 22 | 5 | 3 (40) | 18 | 63 | ND | ND |
| A7 | M | 53 | 25 | 26 | 15.8 (39) | 19 | 1100 | 19 | 262 |
| A8 | F | 39 | 18 | 13 | 8.2 (37) | 17 | 1187 | 20 | 4866 |
| A9 | F | 26 | 38 | 141 | 100 (29) | 63 | 740 | 59 | 3745 |
| A10 | F | 30 | 42 | 195 | 151 (23) | 30 | 849 | 2 | 210 |

[a]Maximal tumor diameter was evaluated by MRI.
[b]SSTR2 and SSTR5 mRNA expression in each adenoma is shown. Results are expressed as picograms of SSTR mRNA per picograms GAPDH mRNA.
[c]Mean GH values were determined 2–6 h after acute octreotide challenge (200 μg, sc). Percent inhibition vs. GH basal value is indicated in parentheses.
ND, Not done.
Cases 1 and 3 were presented in a previous study (Jaquet, P., et al., J. Clin Endocrinol Metab. 85: 781–792).

TABLE 2

Human somatostatin receptor subtype specificity of SRIF-14 and somatostatin analogs

| Compound | SSTR binding affinity (IC$_{50}$, mmol/L) | | | | |
|---|---|---|---|---|---|
| | hSSTR1 | hSSTR2 | hSSTR3 | hSSTR4 | hSSTR5 |
| Somatostatin-14 | 1.95 | 0.25 | 1.2 | 1.7 | 1.4 |
| Octreotide | 1140 | 0.6 | 34.5 | 7030 | 7 |
| Lanreotide | 2129 | 0.7 | 98 | 1826 | 12.7 |
| Compound A | 6016 | 0.19 | 26.8 | 3897 | 9.8 |
| Compound B | 12 | 28 | 5.5 | 36 | 0.42 |
| Formula (I) | 1020 | 0.29 | 133 | >1000 | 0.67 |

Data from radioligand binding assays to membranes from transfected CHO-K1 cell expressing the different human SSTR (hSSTR) subtypes. Correlation between octreotide sensitivity and SSTR2 and SSTR5 subtype mRNA expression in acromegaly The degree of GH inhibition by SRIF-14 in vitro and the levels of SSTR2 mRNA expression have been previously shown to be highly correlated (Jaquet P, et al. 2000, J Clin Endocrinol Metab. 85:781–792.). In the present series the degree of GH inhibition in patients, as evaluated by acute octreotide test, was also highly correlated to the level of SSTR2 mRNA expression (P<0.009; Table 1).

In five adenomas (A1–A5) highly sensitive to octreotide, the mean SSTR2 expression was 222±61 pg/pg GAPDH. When the same analysis was made in four of five (A7–A10) adenomas from partial octreotide responders, the mean SSTR2 mRNA expression was much lower (25±12 pg/pg GAPDH). The five adenomas from octreotide-responsive patients expressed SSTR5 mRNA at an equivalent level (SSTR2/SSTR5 mRNA ratio, 0.9±0.3). In contrast, adenomas from the four partial octreotide responders with low SSTR2 mRNA expression expressed high levels of SSTR5 mRNA (2271±1197 pg/pg GAPDH). Thus, these data establish two patterns of mRNA expression in the GH-secreting tumors. The octreotide-sensitive adenomas equally express both SSTR2 and SSTR5 mRNA, whereas in the adenomas that were poorly responsive to octreotide, the loss of SSTR2 mRNA contrasted with a 30-fold higher expression of SSTR5 vs. SSTR2 mRNA.

Effects of SSTR2- and SSTR5-Preferential Agonists on GH Secretion

In this series of experiments, the dose-response inhibition of GH release was examined with $10^{-13}$–$10^{-9}$ mol/L concentrations of SRIF-14; the SSTR2-preferential compound, Compound A; and the SSTR5 preferential compound, Compound B. Among the 10 adenoma cell cultures, 2 patterns of responses to SSTR2- and SSTR5-preferential analogs were observed. In cultures from the 5 octreotide-sensitive tumors (A1–A5), the SSTR2-preferential compound, Compound A, produced a maximal 41±7% mean GH suppression at a 0.1 nmol/L concentration, with an EC$_{50}$ of 3±2 pmol/L. A similar dose-response inhibition of GH release was obtained with SRIF-14. In contrast, the SSTR5-preferential compound, Compound B, produced a maximal inhibition of GH release only at 10 nmol/L (EC$_{50}$=800±350 pmol/L). This discrepancy between the results obtained with Compound A and Compound B can be explained on the basis of the binding affinities of Compound B, which is preferential for SSTR5, but at high concentrations behaves as a weak SSTR2 agonist. Thus, in the tumor cells from full octreotide responders, the GH-suppressive effect of somatostatin was mediated through only the SSTR2 subtype. In the second class of GH-secreting tumors that were partially responsive to octreotide (A6–A10), maximal GH suppression was equally achieved by SRIF-14 and the SSTR5-preferential agonist, Compound B. In these 5 adenoma cell cultures, Compound A was slightly less potent than Compound B (maximal GH suppression, 31±5% and 38±7%, respectively). The EC$_{50}$ values achieved with Compound B and Compound A were 25±13 and 47±18 pmol/L, respectively. These data indicate that in tumor cells that are partially responsive to octreotide, the GH-suppressive effect of SRIF is mediated through both the SSTR5 and SSTR2 subtypes.

Compound of Formula (I) vs. Octreotide in the Octreotide-Sensitive and Octreotide Partially Sensitive Tumors In the five octreotide-sensitive tumors in which the GH-suppressive effect of SRIF was mediated through the SSTR2 subtype, the effects of the SSTR2- plus SSTR5-selective compound of formula (I), and octreotide on GH secretion were examined using $10^{-3}$–$10^{-8}$ mol/L of each compound. The dose-response inhibition curves of GH release induced by the compound of formula (I) and octreotide were parallel ($EC_{50}$=3±3 and 55±15 pmol/L, respectively). At nanomolar concentrations, the mean maximal GH suppressions induced by the compound of formula (I) and octreotide were 44±5% and 36±7%, respectively. These results show that when the GH-suppressive effect is mediated through the SSTR2 subtype, native SRIF and the compound of formula (I) are similarly efficacious in suppressing GH secretion. As expected from the binding affinities for SSTR2, the compound of formula (I) was slightly more potent than octreotide.

The same dose-response inhibitions of GH release by the compound of formula (I) and octreotide were examined in adenoma cell cultures from the five (A6–A10) octreotide partially responsive tumors. The dose-related pattern of GH inhibition induced by octreotide ($EC_{50}$=200±145 pmol/L) was markedly distinct from that induced by the compound of formula (I) ($EC_{50}$=50±33 pmol/L). The compound of formula (I) at a concentration of 10 nM induced a greater suppression of GH than octreotide at the same concentration (44±5% vs. 26±7%, respectively; P<0.014). These results demonstrate that in the subclass of GH-secreting tumors responsive to both SSTR2- and SSTR5-preferential agonists (octreotide partial responders), the biselective compound of formula (I) analog can achieve greater GH suppression than SSTR2-preferential drugs, such as octreotide.

Comparison Between Compound of Formula (I) and the Combination of SSTR2- and SSTR5-Preferential Agonists In the five cell cultures from adenomas equally sensitive to the SSTR2- and SSTR5- preferential agonists (octreotide partial responders), the dose-response inhibition of GH release by the compound of formula (I) was compared with that induced by a combination of the SSTR2 preferential agonist, Compound A, and the SSTR5 preferential agonist, Compound B, at equimolar doses. Similar maximal levels of GH suppression (44±5%) were achieved by Compound of formula (I) and the combination of Compound A and Compound B. The dose-response inhibitions of GH release induced by the two treatments were parallel. Considering their respective $IC_{50}$ values for both the SSTR2 and SSTR5 subtypes, the combination of Compound A and Compound B was slightly more potent in suppressing GH secretion than the biselective agonist Compound of formula (I).

Effect of Compound of Formula (I) vs. Octreotide on PRL Release

In five tumor cell cultures (A1, A2, A7, A9, and A10), both PRL and GH were secreted into the culture medium. A dose-response inhibition of PRL secretion by SRIF-14 and by the different SRIF analogs was observed in all tumors, with a significant maximal inhibition of PRL release. The dose-related inhibition of PRL release was similarly achieved with increasing concentrations of SRIF-14 and the SSTR5-preferring compound, Compound B. The SSTR2-preferring compound, Compound A, was partially effective in suppressing PRL secretion (mean maximal PRL inhibition, 34±5% vs. 52±6%, respectively, for Compound A and Compound B). Compared with octreotide, the biselective compound of formula (I) was more effective in suppressing PRL secretion. The mean maximal PRL suppressions at 10 nmol/L compound of formula (I) and octreotide were 51±5% and 34±7%, respectively (P<0.045). These results in mixed GH-/ PRL-secreting tumors indicate a better PRL-suppressive effect of either the SSTR5-preferring compound or the bispecific SSTR2 and SSTR5 compound compared with the agonists preferential for SSTR2 alone.

It is to be understood that while the invention has been described in conjunction with the detailed description thereof, that the foregoing description is intended to illustrate and not to limit the scope of the invention. Other aspects, advantages, and modifications are within the claims. Also, the contents of each references cited herein is incorporated by reference in its entirety.

What is claimed is:

1. A compound of the formula (I),

D-Phe-c(Cys-Tyr(I)-D-Trp-Lys-Val-Cys)-Thr-NH$_2$, wherein the phenyl ring of said Tyr is iodinated at the 3 or 5 position or a pharmaceutically acceptable salt thereof.

* * * * *